(12) United States Patent
Fukuyama

(10) Patent No.: US 6,617,143 B1
(45) Date of Patent: Sep. 9, 2003

(54) POLYPEPTIDES HAVING GLUCANOTRANSFERASE ACTIVITY AND NUCLEIC ACIDS ENCODING SAME

(75) Inventor: Shiro Fukuyama, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/687,360

(22) Filed: Oct. 13, 2000

Related U.S. Application Data

(60) Provisional application No. 60/166,539, filed on Nov. 18, 1999, and provisional application No. 60/160,903, filed on Oct. 22, 1999.

(30) Foreign Application Priority Data

Oct. 20, 1999 (DK) .......................................... 1999 01501
Nov. 15, 1999 (DK) .......................................... 1999 01641

(51) Int. Cl.[7] ............................ C12P 15/09; C12N 9/00; C12N 9/10; C12N 1/20; C12N 15/00; D06M 16/00
(52) U.S. Cl. ...................... 435/193; 435/69.2; 435/183; 435/252.3; 435/320.1; 435/262; 435/263; 536/23.2; 536/23.7; 510/114
(58) Field of Search ................. 435/69.1, 183, 435/193, 252.3, 262, 263; 536/23.2, 23.7; 510/114

(56) References Cited

U.S. PATENT DOCUMENTS 6,015,783 A * 1/2000 von der Osten et al. .... 510/392

FOREIGN PATENT DOCUMENTS

EP 0 884 384 A2 12/1998

OTHER PUBLICATIONS

Kaneko et al. PIR Database Accession No. S74648, Apr. 25, 1997.*

Kitahata et al., Agric. Biol. Chem., 53 (10), 2653–2659, 1989.

Peat et al., J. Chem. Soc. 1956, 44–53.

Terada et al., Applied and Environmental Microbiology, vol. 65, No. 3, pp 910–915 (1999).

Takaha et al., The Journal of Biological Chemistry, vol. 208, No. 2, pp. 1881–1895 (1998).

\* cited by examiner

*Primary Examiner*—Rebecca E. Prouty
*Assistant Examiner*—Manjunath N. Rao
(74) *Attorney, Agent, or Firm*—Elias Lambiris; Jason Garbell

(57) ABSTRACT

The present invention relates to isolated polypeptides having glucanotransferase activity and isolated nucleic acid sequences encoding the polypeptides. The invention also relates to nucleic acid constructs, vectors, and host cells comprising the nucleic acid sequences as well as methods for producing and using the polypeptides.

21 Claims, 4 Drawing Sheets

SEQUENCE LISTING

<160> NUMBER OF SEQ ID NOS: 6

<210> SEQ ID NO 1
<211> LENGTH: 1503
<212> TYPE: DNA
<213> ORGANISM: Thermus rubens
<220> FEATURE:
<221> NAME/KEY: CDS
<222> LOCATION: (1)...(1503)

<400> SEQUENCE: 1

| | | | | | | | | | | | | | | | | |
|---|---|---|---|---|---|---|---|---|---|---|---|---|---|---|---|---|
| atg | caa | ctc | caa | cgc | gct | ttt | gga | att | ttg | ctc | cac | ccc | acc | agt | ttt | 48 |
| Met | Gln | Leu | Gln | Arg | Ala | Phe | Gly | Ile | Leu | Leu | His | Pro | Thr | Ser | Phe | |
| 1 | | | | 5 | | | | | 10 | | | | | 15 | | |
| ccg | ggt | cgc | tgg | ggg | att | ggg | gct | ctg | ggc | cgc | gag | gcc | gag | cgg | ttt | 96 |
| Pro | Gly | Arg | Trp | Gly | Ile | Gly | Ala | Leu | Gly | Arg | Glu | Ala | Glu | Arg | Phe | |
| | | | 20 | | | | | 25 | | | | | 30 | | | |
| ttg | gac | tgg | ctg | gcc | gat | gcg | gga | gcc | cgc | tgg | tgg | cag | gtc | tta | ccg | 144 |
| Leu | Asp | Trp | Leu | Ala | Asp | Ala | Gly | Ala | Arg | Trp | Trp | Gln | Val | Leu | Pro | |
| | | 35 | | | | | 40 | | | | | 45 | | | | |
| ctg | ggc | cct | acc | agt | tac | ggc | gac | tcg | ccg | tac | cag | tcc | ttc | tcg | gct | 192 |
| Leu | Gly | Pro | Thr | Ser | Tyr | Gly | Asp | Ser | Pro | Tyr | Gln | Ser | Phe | Ser | Ala | |
| | 50 | | | | | 55 | | | | | 60 | | | | | |
| ttt | gcc | ggt | aac | ccg | tat | ttg | gtt | gac | ccc | gag | atg | ctg | att | gaa | aaa | 240 |
| Phe | Ala | Gly | Asn | Pro | Tyr | Leu | Val | Asp | Pro | Glu | Met | Leu | Ile | Glu | Lys | |
| 65 | | | | | 70 | | | | | 75 | | | | | 80 | |
| ggc | tgg | ctg | gaa | caa | agc | gaa | gcg | ccc | ccg | ccg | tat | ccg | acc | cag | cgc | 288 |
| Gly | Trp | Leu | Glu | Gln | Ser | Glu | Ala | Pro | Pro | Pro | Tyr | Pro | Thr | Gln | Arg | |
| | | | | 85 | | | | | 90 | | | | | 95 | | |
| gtg | gat | tat | ggc | tgg | ctt | tac | cag | acc | cgc | tgg | ccc | ctg | ttg | cgg | cgg | 336 |
| Val | Asp | Tyr | Gly | Trp | Leu | Tyr | Gln | Thr | Arg | Trp | Pro | Leu | Leu | Arg | Arg | |
| | | | 100 | | | | | 105 | | | | | 110 | | | |
| gct | ttc | gcg | ggg | ttt | cgg | gca | agg | gct | tcg | gcc | cag | gat | aag | acc | cga | 384 |
| Ala | Phe | Ala | Gly | Phe | Arg | Ala | Arg | Ala | Ser | Ala | Gln | Asp | Lys | Thr | Arg | |
| | | 115 | | | | | 120 | | | | | 125 | | | | |
| ctg | gaa | gcc | ttt | atc | gag | gcc | gag | cgc | ttc | tgg | ctg | gaa | gac | tat | gcg | 432 |
| Leu | Glu | Ala | Phe | Ile | Glu | Ala | Glu | Arg | Phe | Trp | Leu | Glu | Asp | Tyr | Ala | |
| | 130 | | | | | 135 | | | | | 140 | | | | | |
| ctc | ttt | atg | gcc | ctc | aag | acc | cgg | ttt | gac | ggc | aag | ccc | tgg | aac | gag | 480 |
| Leu | Phe | Met | Ala | Leu | Lys | Thr | Arg | Phe | Asp | Gly | Lys | Pro | Trp | Asn | Glu | |
| 145 | | | | | 150 | | | | | 155 | | | | | 160 | |
| tgg | agc | ccc | gag | ctg | cgc | gac | cgt | gaa | ccg | gct | gcc | ctg | gcc | agg | gcc | 528 |
| Trp | Ser | Pro | Glu | Leu | Arg | Asp | Arg | Glu | Pro | Ala | Ala | Leu | Ala | Arg | Ala | |
| | | | | 165 | | | | | 170 | | | | | 175 | | |
| cgt | gag | gag | ctg | gcc | gag | gag | gtg | gcc | ctt | tac | gag | tgg | att | cag | tgg | 576 |
| Arg | Glu | Glu | Leu | Ala | Glu | Glu | Val | Ala | Leu | Tyr | Glu | Trp | Ile | Gln | Trp | |
| | | | 180 | | | | | 185 | | | | | 190 | | | |
| ctt | ttt | tat | ctg | gaa | tgg | ggc | cag | acc | aag | gcc | tat | gcc | gaa | tcc | aag | 624 |
| Leu | Phe | Tyr | Leu | Glu | Trp | Gly | Gln | Thr | Lys | Ala | Tyr | Ala | Glu | Ser | Lys | |
| | | 195 | | | | | 200 | | | | | 205 | | | | |
| ggg | att | cag | att | atc | ggc | gat | atg | ccc | atc | ttt | gtg | gcc | ttc | gat | tcc | 672 |
| Gly | Ile | Gln | Ile | Ile | Gly | Asp | Met | Pro | Ile | Phe | Val | Ala | Phe | Asp | Ser | |
| | 210 | | | | | 215 | | | | | 220 | | | | | |
| tca | gat | gtc | tgg | gcc | aac | ccg | cag | tac | ttc | tac | ctc | gag | gcc | gat | ggc | 720 |
| Ser | Asp | Val | Trp | Ala | Asn | Pro | Gln | Tyr | Phe | Tyr | Leu | Glu | Ala | Asp | Gly | |
| 225 | | | | | 230 | | | | | 235 | | | | | 240 | |
| aac | ccc | acg | gtg | gtg | gcg | ggc | gtt | ccg | cgg | gac | tac | ttc | tcc | gaa | acc | 768 |
| Asn | Pro | Thr | Val | Val | Ala | Gly | Val | Pro | Arg | Asp | Tyr | Phe | Ser | Glu | Thr | |
| | | | | 245 | | | | | 250 | | | | | 255 | | |

```
ggc cag ctc tgg ggc aat ccg ctc tat cgc tgg gat gtg atg gaa agg     816
Gly Gln Leu Trp Gly Asn Pro Leu Tyr Arg Trp Asp Val Met Glu Arg
            260                 265                 270 gac aac ttt gcc tgg tgc att gcc cgc ata agg cag tcg ctc aag cag     864
Asp Asn Phe Ala Trp Cys Ile Ala Arg Ile Arg Gln Ser Leu Lys Gln
        275                 280                 285 tgc cac ctg gtg cgc atc gac cac ttc cgc ggg ttt gaa gcc tac tgg     912
Cys His Leu Val Arg Ile Asp His Phe Arg Gly Phe Glu Ala Tyr Trp
290                 295                 300 gag gtt ccg ttt ggc cgg ccc aat gct gtg gag ggg cgc tgg gtc aaa     960
Glu Val Pro Phe Gly Arg Pro Asn Ala Val Glu Gly Arg Trp Val Lys
305                 310                 315                 320 gcc cca ggg gag aag ctg ttt gct gcg gtg cgg gcc caa ctg agc gat    1008
Ala Pro Gly Glu Lys Leu Phe Ala Ala Val Arg Ala Gln Leu Ser Asp
                325                 330                 335 gcg ccc atc att gcc gaa gac ctg ggg gtg atc acc ccc gag gtg gag    1056
Ala Pro Ile Ile Ala Glu Asp Leu Gly Val Ile Thr Pro Glu Val Glu
            340                 345                 350 gct ttg cgc gat ggc ttc ggg ttc ccc ggc atg aag att ttg cag ttt    1104
Ala Leu Arg Asp Gly Phe Gly Phe Pro Gly Met Lys Ile Leu Gln Phe
        355                 360                 365 gct ttt tcc ggt gag gac aac gcc ttt ttg ccc cac aac tac ccc gcg    1152
Ala Phe Ser Gly Glu Asp Asn Ala Phe Leu Pro His Asn Tyr Pro Ala
370                 375                 380 cac ggc aat gtg gtg gtg tac agc gga acc cac gac aac gac acc acc    1200
His Gly Asn Val Val Val Tyr Ser Gly Thr His Asp Asn Asp Thr Thr
385                 390                 395                 400 ctg gga tgg ttc cgc acc gcg ccg gag gcc gag cgg gcc ttc atg cgg    1248
Leu Gly Trp Phe Arg Thr Ala Pro Glu Ala Glu Arg Ala Phe Met Arg
                405                 410                 415 gcc tac ctg gcc cgc tat ggc atc cgt tgt ttg tcg gaa tac gag gtc    1296
Ala Tyr Leu Ala Arg Tyr Gly Ile Arg Cys Leu Ser Glu Tyr Glu Val
            420                 425                 430 gcg ggc gct ttg atc gag ctg gcc ttc aaa agc ccg gcc aag ctg gct    1344
Ala Gly Ala Leu Ile Glu Leu Ala Phe Lys Ser Pro Ala Lys Leu Ala
        435                 440                 445 att gtg cct ttg cag gac gtg ctg ggg ctg ggc ccc gag gcc cgc atg    1392
Ile Val Pro Leu Gln Asp Val Leu Gly Leu Gly Pro Glu Ala Arg Met
450                 455                 460 aac ttc ccc gga cgg ctg ggg gac aac tgg gcg tgg cgc tac gcc gaa    1440
Asn Phe Pro Gly Arg Leu Gly Asp Asn Trp Ala Trp Arg Tyr Ala Glu
465                 470                 475                 480 ggc gac ctc gag ccc ggt ctg gcc gcg gga ctg cgg gcc ctg gcc gag    1488
Gly Asp Leu Glu Pro Gly Leu Ala Ala Gly Leu Arg Ala Leu Ala Glu
                485                 490                 495 gcc agc cag cgc gct                                                 1503
Ala Ser Gln Arg Ala
            500

<210> SEQ ID NO 2
<211> LENGTH: 501
<212> TYPE: PRT
<213> ORGANISM: Thermus rubens

<400> SEQUENCE: 2

Met Gln Leu Gln Arg Ala Phe Gly Ile Leu Leu His Pro Thr Ser Phe
 1               5                  10                  15

Pro Gly Arg Trp Gly Ile Gly Ala Leu Gly Arg Glu Ala Glu Arg Phe
            20                  25                  30

Leu Asp Trp Leu Ala Asp Ala Gly Ala Arg Trp Trp Gln Val Leu Pro
```

```
                    35                  40                  45
Leu Gly Pro Thr Ser Tyr Gly Asp Ser Pro Tyr Gln Ser Phe Ser Ala
 50                  55                  60
Phe Ala Gly Asn Pro Tyr Leu Val Asp Pro Glu Met Leu Ile Glu Lys
65                   70                  75                  80
Gly Trp Leu Glu Gln Ser Glu Ala Pro Pro Tyr Pro Thr Gln Arg
                 85                  90                  95
Val Asp Tyr Gly Trp Leu Tyr Gln Thr Arg Trp Pro Leu Leu Arg Arg
                100                 105                 110
Ala Phe Ala Gly Phe Arg Ala Arg Ala Ser Ala Gln Asp Lys Thr Arg
            115                 120                 125
Leu Glu Ala Phe Ile Glu Ala Glu Arg Phe Trp Leu Glu Asp Tyr Ala
        130                 135                 140
Leu Phe Met Ala Leu Lys Thr Arg Phe Asp Gly Lys Pro Trp Asn Glu
145                 150                 155                 160
Trp Ser Pro Glu Leu Arg Asp Arg Glu Pro Ala Ala Leu Ala Arg Ala
                165                 170                 175
Arg Glu Glu Leu Ala Glu Val Ala Leu Tyr Glu Trp Ile Gln Trp
            180                 185                 190
Leu Phe Tyr Leu Glu Trp Gly Gln Thr Lys Ala Tyr Ala Glu Ser Lys
        195                 200                 205
Gly Ile Gln Ile Ile Gly Asp Met Pro Ile Phe Val Ala Phe Asp Ser
    210                 215                 220
Ser Asp Val Trp Ala Asn Pro Gln Tyr Phe Tyr Leu Glu Ala Asp Gly
225                 230                 235                 240
Asn Pro Thr Val Val Ala Gly Val Pro Arg Asp Tyr Phe Ser Glu Thr
                245                 250                 255
Gly Gln Leu Trp Gly Asn Pro Leu Tyr Arg Trp Asp Val Met Glu Arg
            260                 265                 270
Asp Asn Phe Ala Trp Cys Ile Ala Arg Ile Arg Gln Ser Leu Lys Gln
        275                 280                 285
Cys His Leu Val Arg Ile Asp His Phe Arg Gly Phe Glu Ala Tyr Trp
    290                 295                 300
Glu Val Pro Phe Gly Arg Pro Asn Ala Val Glu Gly Arg Trp Val Lys
305                 310                 315                 320
Ala Pro Gly Glu Lys Leu Phe Ala Ala Val Arg Ala Gln Leu Ser Asp
                325                 330                 335
Ala Pro Ile Ile Ala Glu Asp Leu Gly Val Ile Thr Pro Glu Val Glu
            340                 345                 350
Ala Leu Arg Asp Gly Phe Gly Phe Pro Gly Met Lys Ile Leu Gln Phe
        355                 360                 365
Ala Phe Ser Gly Glu Asp Asn Ala Phe Leu Pro His Asn Tyr Pro Ala
    370                 375                 380
His Gly Asn Val Val Tyr Ser Gly Thr His Asp Asn Asp Thr Thr
385                 390                 395                 400
Leu Gly Trp Phe Arg Thr Ala Pro Glu Ala Glu Arg Ala Phe Met Arg
                405                 410                 415
Ala Tyr Leu Ala Arg Tyr Gly Ile Arg Cys Leu Ser Glu Tyr Glu Val
            420                 425                 430
Ala Gly Ala Leu Ile Glu Leu Ala Phe Lys Ser Pro Ala Lys Leu Ala
        435                 440                 445
Ile Val Pro Leu Gln Asp Val Leu Gly Leu Gly Pro Glu Ala Arg Met
    450                 455                 460
```

```
Asn Phe Pro Gly Arg Leu Gly Asp Asn Trp Ala Trp Arg Tyr Ala Glu
465                 470                 475                 480

Gly Asp Leu Glu Pro Gly Leu Ala Ala Gly Leu Arg Ala Leu Ala Glu
                485                 490                 495

Ala Ser Gln Arg Ala
            500

<210> SEQ ID NO 3
<211> LENGTH: 23
<212> TYPE: DNA
<213> ORGANISM: Artificial Sequence
<220> FEATURE:
<223> OTHER INFORMATION: Primer
<221> NAME/KEY: misc_feature
<222> LOCATION: 3,9,12,21
<223> OTHER INFORMATION: n = inosine

<400> SEQUENCE: 3
ggngayatnc cnathtayrt ngs                                            23

<210> SEQ ID NO 4
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: 10,13,16
<223> OTHER INFORMATION: n = inosine

<400> SEQUENCE: 4
rttrtcrtgn gtnccngtrt a                                              21

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
gcgccatgga actccaacgc gcttttg                                        27

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
gcgtctagat caagcgcgct ggctggcctc                                     30
```

POLYPEPTIDES HAVING GLUCANOTRANSFERASE ACTIVITY AND NUCLEIC ACIDS ENCODING SAME

CROSS-REFERENCE TO RELATED APPLICATIONS

This application claims priority under 35 U.S.C. 119 of Danish applications PA 1999 01501 filed Oct. 20, 1999 and PA 1999, 01641 filed Nov. 15, 1999, and of U.S. Provisionals No. 60/160,903 filed Oct. 22, 1999 and No. 60/166,539 filed Nov. 18, 1999, the contents of which are fully incorporated herein by reference.

FIELD OF THE INVENTION

The present invention relates to isolated polypeptides having glucanotransferase activity and isolated nucleic acid sequences encoding the polypeptides. The invention also relates to nucleic acid constructs, vectors, and host cells comprising the nucleic acid sequences as well as methods for producing and using the polypeptides.

DESCRIPTION OF THE RELATED ART

4-α-glucanotransferases (EC. 2.4.1.25) catalyzes the reaction of transferring an α-glucan chain from one α-glucan molecule to another (or to glucose). Glucanotransferases are widely distributed in microorganisms (e.g. *E. coli*) and plant tissues such as potato tubers, germinating barley seeds, sweet potato and spinach.

Recently, glucanotransferases have been found to be capable of catalyzing an intramolecular reaction of an α-glucan. For example, it has been reported that glucanotransferase is capable of catalyzing an intramolecular transglycosylation reaction (cyclization reaction) of amylose, thereby synthesizing cycloamylose having a degree of polymerization (hereinafter "DP") of 17 or more.

Glucanotransferases can be applied for various industrial purposes. As an example, a glucanotransferase can be utilized in processing an α-glucan for the production of a cyclic glucan. In the case for using an enzyme for an industrial purpose, the reaction is desirably conducted at a temperature as high as possible (about 60° C. or higher) due to the fact that an α-glucan, i.e. the substrate, is thereby prevented from retrogradation and, at the same time, contamination of the system by microorganism is avoided, or at least reduced.

In general, only glucanotransferases (amylomaltases) having a high activity in a moderate temperature interval (typically from about 30 to 45° C.) have been isolated, see, for example, *Agric. Biol. Chem.* 53, 2653–2659 (1989) and *J. Chem. Soc.*, 44–53 (1956). More recently, a novel heat-resistant glucanotransferase (amylomaltase) also capable of generating a cyclic glucan has been described in EP 0 884 384 A2.

SUMMARY OF THE INVENTION

Thus, in a first aspect the present invention relates to an isolated polypeptide having glucanotransferase activity, selected from the group consisting of:
  (a) a polypeptide having an amino acid sequence which has at least 65% identity with the amino acid sequence shown as amino acids 1 to 501 of SEQ ID NO:2;
  (b) a polypeptide which is encoded by a nucleic acid sequence which hybridizes under low stringency conditions with
    (i) a complementary strand of the nucleic acid sequence shown as nucleotides i1 to 1503 of SEQ ID NO:1, or
    (ii) a subsequence of (i) of at least 100 nucleotides;
  (c) an allelic variant of (a) or (b);
  (d) a polypeptide encoded by the glucanotransferase encoding part of the DNA sequence cloned into a plasmid present in *Escherichia coli* DSM 13049, or a variant thereof having at least 65% identity to said polypeptide; and
  (e) a fragment of said polypeptide having glucanotransferase activity.

In a second aspect the present invention relates to an isolated nucleic acid sequence comprising a nucleic acid sequence which encodes for the polypeptide of the invention.

In a third aspect, the present invention relates to an isolated nucleic acid sequence encoding a polypeptide having glucanotransferase activity, selected from the group consisting of:
  (a) a nucleic acid sequence having at least 70% identity with the nucleic acid sequence shown as nucleotides 1 to 1503 of SEQ ID NO:1;
  (b) a nucleic acid sequence which hybridizes under low stringency conditions with
    (i) a complementary strand of the nucleic acid sequence shown as nucleotides 1 to 1503 of SEQ ID NO:1, or
    (ii) a subsequence of (i) of at least 100 nucleotides;
  (c) an allelic variant of (a) or (b);
  (d) the glucanotransferase encoding part of the DNA sequence which has been cloned into a plasmid present in *Escherichia coli* DSM 13049, or a variant thereof having at least 70% identity to said DNA sequence; and
  (e) a subsequence of (a), (b), (c), or (d), wherein the subsequence encodes a polypeptide fragment which has glucanotransferase activity;
or an isolated nucleic acid sequence which is the complementary strand of (a), (b), (c), (d) or (e).

In a fourth aspect the present invention a nucleic acid construct comprising the nucleic acid sequence of the invention operably linked to one or more control sequences capable of directing the expression of the polypeptide in a suitable expression host.

In a fifth aspect the present invention relates to a recombinant expression vector comprising the nucleic acid construct of the invention, a promoter, and transcriptional and translational stop signals.

In a sixth aspect the present invention relates to a recombinant host cell comprising the nucleic acid construct of the invention.

The present invention also relates to methods for producing the polypeptide of the invention; to methods for producing foods and use of the polypeptide of the invention for producing foods as well as to detergent compositions comprising the polypeptide of the invention.

DETAILED DESCRIPTION OF THE INVENTION

Definitions

Figure 1:
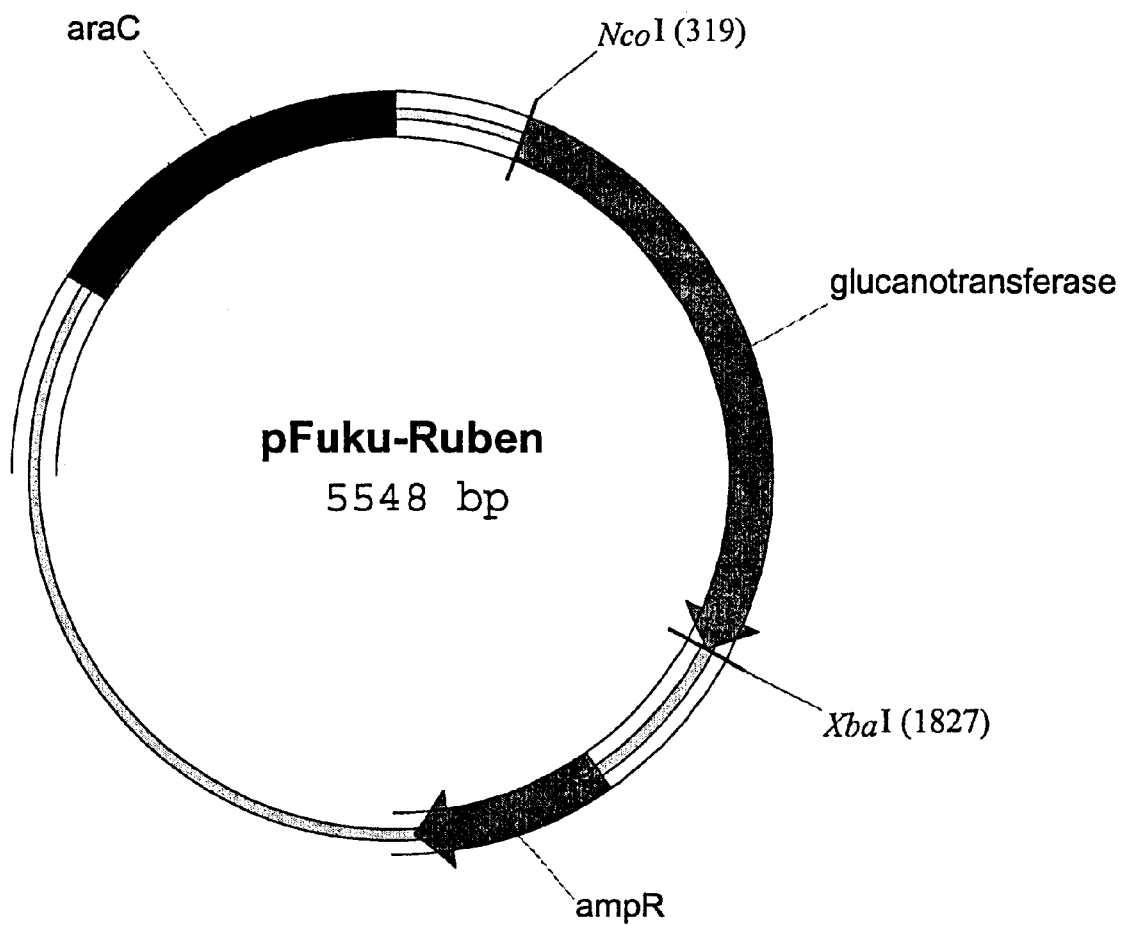
FIG. 1 illustrates the plasmid pFUKU-Ruben.

When used herein the term "α-glucan" refers to an α-1,4-glucan (a polysaccharide having a chain structure containing maltose as a constitutive disaccharide unit) or an α-1,4-glucan having an α-1,6-branched structure. Examples of the α-glucan include amylose, amylopectin, starches, glycogen, waxy starches, high amylose starches, soluble starches, dextrins, hydrolyzed starch products, and amylopectins enzymatically synthesized with phosphorylase.

In the present context the term "cyclic glucan" is intended to mean a cyclic α-1,4-glucan having only α-1,4-glucosidic bonds and a branched cyclic glucan having both α-1,4-glucosidic bonds and α-1,6-glucosidic bonds. The term "branched" is intended to mean that the α-glucan (whether cyclic or not) has at least one glucosidic bond different from an α-1,4-bond. Examples of branched cyclic glucans include an innner branched cyclic glucan containing a branch structure having an α-1,6-bond in a cyclic structure, and an outer branched cyclic glucan containing a non-cyclic structure portion in addition to a cyclic structure.

When used herein the term "glucanotransferase activity" or "activity" refers to the activity of the polypeptide measured by the amount of glucose generated when the polypeptide acts on a solution containing: 0.86% (w/v) maltotriose and 20 mM sodium phosphate (pH 7.0) at 65° C. for 10 minutes. One unit enzyme activity is defined as the amount of polypeptide which releases 1 μmol glucose per minute using the above-mentioned conditions.

As defined herein, an "isolated polypeptide" is a polypeptide which is essentially free of other polypeptides. Thus, an "isolated polypeptide" should be at least about 20% pure, preferably at least about 40% pure, more preferably at least about 60% pure, even more preferably at least about 80% pure, most preferably at least about 90% pure, in particular at least about 95% pure, as determined by SDS-PAGE.

The term "isolated nucleic acid sequence" as used herein refers to a nucleic acid sequence which is essentially free of other nucleic acid sequences. Thus, an "isolated nucleic acid sequence" should be at least about 20% pure, preferably at least about 40% pure, more preferably at least about 60% pure, even more preferably at least about 80% pure, and most preferably at least about 90% pure, as determined by agarose electrophoresis.

In the present context the term "expression" includes any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term "nucleic acid construct" is synonymous with the term "expression cassette" when the nucleic acid construct contains all the control sequences required for expression of a coding sequence of the present invention.

The term "coding sequence" is defined herein as a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

When used herein the term "control sequence" includes all components which are necessary or advantageous for the expression of a polypeptide of the present invention.

The term "operably linked" is defined herein as a configuration in which a control sequence is appropriately placed at a position relative to the coding sequence of the DNA sequence such that the control sequence directs the expression of a polypeptide.

When used herein the term "host cell" encompasses any progeny of a parent cell that is not identical to the parent cell due to mutations that occur during replication.

Use of Polypeptides Having Glucanotransferase Activity for Improving Food

The polypeptide of the present invention catalyzes the cyclization reaction of starch by acting on starch in food. As a result, the molecular size of the starch in the food is reduced and a cyclic glucan is produced. The cyclic glucan produced by this reaction has low viscosity, high solubility, the ability to suppress retrogradation of starch as well as the ability to include various substances. Thus, food can be improved by using the polypeptide of the present invention. Typically, the polypeptide of the invention is allowed to act on the starch in food to accumulate a cyclic glucan, whereby the physical properties of the food, such as improved stability during storage, and mouthfeel may be improved. The cyclic glucan is easily degraded. into glucose in the organism and, cosequently, the cyclic glucan has good digestability and a high energy conversion efficiency.

The polypetide of the present invention an be used for improving a wide range of starch-containing foods, including Japanese desserts (e.g. bracken rice cakes, bean cakes, rice cakes, rice jellies, and rice bean cakes), snacks (e.g. Japanese crackers, rice crackers, potato chips, and other snacks), wheat products (e.g. breads, pies, pizzas, cakes, cookies, biscuits, and crackers), noodles (e.g. wheat noodles, buckwheat noodles, Chineese noodles, and pastas such as spaghetti and macaroni), gyoza skins, shumai skins, processed seafooods (e.g. fish sticks and fish-paste cakes), frozen or refrigerated processed foods, weaning foods, baby foods, pet foods, animal feeds, drinks (e.g. sports drinks), sports foods and nutrient supplemental foods.

Rice products, Japanese desserts, snacks, wheat products and noodles, which contain starch in large amounts are examples of preferred foods to which the present invention may be applied. Other examples of preferred foods are frozen or refrigerated processed foods in which the stability during low temperature storage is of importance.

The term "food material" as used herein refers to any material to produce the food described above, and any preparation provided during the process of producing the food.

Whether the food subjected to the polypeptide of the invention is improved can be confirmed by examining whether the molecular size of starch in the food has been reduced as a result of generation of a cyclic glucan.

Food materials, food additive compositions, and food improving agents, respectively, comprising the polypeptide of the invention are also within the scope of the present invention. Examples of food additive compositions include condiments (e.g. soy sauces, soy sauce dips, Worcester sauces, broth bases, stew bases, curry bases, soup bases, mayonnaise, dressings, ketchup, and combined condiments). Examples of food improving agents include anti-retrogradation agents and improving agents for steamed rice.

Detergent Compositions Comprising the Polypeptide Having Glucanotransferase Activity As starch stains, e.g. amylose stains, may be difficult to remove by the present detergents, it is contemplated that the polypeptide of the invention, due to the capability of catalyzing the modification of crystallized starches, such as amylose, into more water-soluble cyclic compounds, may be used in such detergents.

Therefore, the present invention also relates to a cleaning or detergent composition comprising the polypeptide of the invention; to the use of a polypeptide of the invention for removal of starch stains, in particular for removal of amylose stains; as well as to a method for removal of starch stains, in particular for removal of amylose stains, from a hard surface or from laundry, the method comprising contacting the amylose stain-containing hard surface or the amylose stain-containing laundry with the poylpeptide of the invention or with the cleaning or detergent composition of the invention.

Such cleaning and detergent compositions are well described in the art and reference is made to WO 96/34946; WO 97/07202; WO 95/30011 for further description of suitable cleaning and detergent compositions.

Detergent Compositions

The polypeptide of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OXP™, FN2™, and FN3™ (Genencor International Inc.).

Lipases:

Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases:

Suitable arnylases ($\alpha$ and/or $\beta$) include those of bacterial or fungal origin. Chemically modified or protein engineered mutants are included. Amylases include, for example, $\alpha$-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases:

Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the polypeptide (enzyme) of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

The polypeptide of the invention may additionally be incorporated in the detergent formulations disclosed in WO 97/07202 which is hereby incorporated as reference.

Polypeptides Having Glucanotransferase Activity

In a first embodiment of the present invention, the isolated polypeptide has an amino acid sequence which has at least 65% identity with the amino acid sequence shown as amino acids 1 to 501 of SEQ ID NO:2 (i.e., the mature polypeptide). In an interesting embodiment of the invention the polypeptide has at least 70%, at least 75%, at least 80%, at least 85%, at least 90%, at least 95%, at least 96%, at least 97%, at least 98%, or at least 99% identity with the amino acid sequence shown as amino acids 1 to 501 of SEQ ID NO:2 (hereinafter "homologous polypeptides").

In a preferred embodiment, the homologous polypeptides have an amino acid sequence which differs by five amino acids, e.g. by four amino acids, such as by three amino acids, by two amino acids, or by one amino acid from the amino acid sequence shown as amino acids I to 501 of SEQ ID NO:2.

Alignments of sequences and calculation of identity scores were done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA. While the penalty for additional residues in a gap is −2 for proteins and −4 for DNA. Align is from the fasta package version v20u6 (W. R. Pearson and D. J. Lipman (1988), "Improved Tools for Biological Sequence Analysis", *PNAS* 85:2444–2448, and W. R. Pearson (1990) "Rapid and Sensitive Sequence Comparison with FASTP and FASTA" Methods in Enzymology 183:63–98).

Aligning the glucanotransferase having the amino acid sequence shown as amino acids 1 to 501 with the closest prior art, namely the glucanotransferase having the sequence disclosed in EP 0 884 384 and using the methods described above, the following identity percentages are obtained: % identity between amino acid sequences: 62.5%, and % identity between nucleic acid sequences: 65.5%.

Preferably, the polypeptides of the present invention comprise the amino acid sequence shown as amino acids 1 to 501 of SEQ ID NO:2, an allelic variant thereof, or a fragment thereof that has glucanotransferase activity. Obviously, the polypetide of the invention may also consist of the amino acid sequence shown as amino acids 1 to 501 of SEQ ID NO:2.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment of the invention, the isolated polypeptide is encoded by a nucleic acid sequence which hybridizes under low stringency conditions, preferably under medium stringency conditions, more preferably under high stringency conditions with (i) a complementary strand of the nucleic acid sequence shown as nucleotides 1 to 1503 of SEQ ID NO:1, or (ii) a subsequence of (i) of at least 100 nucleotides (J. Sambrook, E. F. Fritsch, and T. Maniatus, 1989, Molecular Cloning, A Laboratory Manual, 2d edition, Cold Spring Harbor, N.Y.).

The subsequence of the complementary strand of the nucleic acid sequence shown as nucleotides 1 to 1503 of SEQ ID NO:1 may be at least 100 nucleotides or preferably at least 200 nucleotides. Moreover, the subsequence should encode a polypeptide fragment which has glucotransferase activity. The polypeptides may also be allelic variants or fragments of the polypeptides that have glucotransferase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having glucanotransferase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having glucanotransferrase activity. Genomic or other DNA from such other organisms may be separated by agarose or polyacrylamide gel electrophoresis, or other separation techniques known by the skilled person. DNA from the libraries or the separated DNA may be transferred to and immobilized on nitrocellulose or other suitable carrier materials. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under low to high stringency conditions. Molecules to which the nucleic acid probe hybridizes under these conditions are detected using X-ray film.

In a second interesting embodiment, the nucleic acid probe is a nucleic acid sequence which encodes the (mature) polypeptide of SEQ ID NO:2, or a subsequence thereof. In a third nteresting embodiment, the nucleic acid probe is SEQ ID NO:1. In a fourth interesting mbodiment, the nucleic acid probe is the mature polypeptide coding region of SEQ ID NO:1. In a fifth interesting embodiment, the nucleic acid probe is the nucleic acid sequence contained in plasmid pFuKu-Ruben which is contained in Eschericlia coli DSM 13049, wherein the nucleic acid sequence encodes a polypeptide having glucanotransferase activity. In a sixth interesting embodiment, the nucleic acid probe is the mature polypeptide coding region contained in plasmid pFuku-Ruben which is contained in Escherichia coli DSM 13049.

For long probes of at least 100 nucleotides in length, low to high stringency conditions are defined as prehybridization and hybridization at 42° C. in 5×SSPE, 0.3% SDS, 200 µg/ml sheared and denatured salmon sperm DNA, and either 25% formamide for low stringency, 35% formamide for medium stringency, or 50% formamide for high stringency, following standard Southern blotting procedures.

For long probes of at least 100 nucleotides in length, the carrier material is finally washed three times each for 15 minutes using 2×SSC, 0.2% SDS preferably at least at 50° C. (low stringency), more preferably at least at 55° C. (medium stringency), even more preferably at least at 65° C. (high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

As indicated above, the polypeptide of the invention may be a polypeptide having an amino acid sequence of SEQ ID NO:2 or the mature poylpeptide thereof, wherein one or more amino acid(s) has (have) been substituted by another (other) amino acid(s), wherein one or more amino acid(s) has (have) been deleted, and/or wherein one more amino acid(s) has (have) been inserted.

Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a very interesting embodiment of the invention, the polypeptide is thermostable, i.e. the polypeptide of the invention retains its enzymatic activity at elevated temperatures.

Therefore, the present inventors have developed a suitable preliminary test which may easily be employed by the skilled person to assess whether an isolated polypeptide may be considered thermostable. Thus, polypeptides, when tested as described herein, which are particular preferred are such polypeptides which retains at least 75% activity, e.g. at least 80% activity, such as at least 85%, preferably at least 90%, such as at least 95%, in particular substantially full activity after incubation at 67° C., preferably after incubation at 70° C. for 10 min in a 20 mM phosphate buffer, pH 7.0. In this connection, it should be understood that 100% activity refers to the glucanotransferase activity described previously, i.e. the above-mentioned percentage values are measured relative to the activity of the polypeptide after incubation at 65° C. for 10 min in a 20 mM phosphate buffer, pH 7.0.

The enzyme should preferably have a pH optimum in the range of from 6 to 8, in particular in the range of from about 6.5 to about 7.5, such as in the range of from about 6.75 to about 7.25, e.g. about 7.

Furthermore, the polypeptide of the invention should preferably, by acting on an α-glucan, such as arnylose, be capable of generating a cyclic glucan by an intramolecular transglycosylation reaction. In addition, the polypeptide of the invention should preferably, by acting on an α-glucan comprising a branched structure, i.e. having an α-1,6-bond, such as amylopectin, be capable generating a branched cyclic glucan.

Moreover, polypeptides which are also considered as being within the scope of the present invention, are isolated polypeptides, preferably in a purified form, having immunochemical identity or partial immunochemical identity to the polypeptide having the amino acid sequence of SEQ ID NO:2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

In general, it is preferred that the polylpeptides of the invention have at least 20% of the glucanotransferase activity of the polypeptide having the amino acid sequence shown as amino acids 1 to 501 of SEQ ID NO:2.

Particular preferred are polypeptides, which have at least 30%, such as at least 40%, e.g. at least 50%, preferably at least 60%, such as at least 70%, e.g. at least 80%, more preferred at least 90%, or at least 95% of the glucanotransferase activity of the polypeptide having the amino acid sequence shown as amino acids 1 to 501 of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

In one interesting embodiment of the invention the polypeptide of the invention may be derived from the genus Thermus, in particular from *Thermus rubens*, such as *Thermus rubens* ATCC 31556.

The present inventors have isolated the gene encoding the polypeptide having glucanotransferase activity from *Thermus rubins* ATCC 31556 and inserted it into *E. coli* DH12S. The *E. coli* strain harboring the gene was deposited according to the Budapest Treaty on the International Recognition of the Deposits of Microorganisms for the Purpose of Patent Procedures on Sep. 20, 1999 at the Deutsche Sammlung von Mikroorganismen und Zellkulturen GmbH, Mascheroder Weg 1 B, D-38124 Braunschweig, Germany, and designated the accession No. DSM 13049.

Therefore, in a further embodiment of the present invention the polypeptide of the invention is a polypeptide encoded by the glucanotransferase encoding part of the DNA sequence cloned into a plasmid present in *Escherichia coli* DSM 13049, or a variant thereof having at least 65% identity to said polypeptide. With respect to the variant it is preferred that the variant polypeptide has at least 70%, at least 75%, at least 80%, at least 85%, at least 90%, at least 95%, at least 96%, at least 97%, at least 98%, or at least 99% identity with the polypeptide encoded by the glucanotransferase encoding part of the DNA sequence cloned into a plasmid present in *Escherichia coli* DSM 13049.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention.

In one interesting embodiment, the nucleic acid sequence has at least 70% identity with the nucleic acid sequence shown as nucleotides 1 to 1503 of SEQ ID NO:1. Preferably, the nucleic acid sequence has at least 75%, at least 80%, at least 85%, at least 90%, at least 95%, at least 96%, at least 97%, at least 98%, or at least 99% identity with the nucleic acid sequence shown as nucleotides 1 to 1503 of SEQ ID NO:1. In another interesting embodiment of the invention the nucleic acid sequence comprises the amino acid sequence shown as nucleotides 1 to 1503 of SEQ ID NO:1, an allelic variant thereof, or a fragment thereof capable of encoding a polypeptide according to the invention. Obviously, the nucleic acid sequence may consist of the amino acid sequence shown as nucleotides 1 to 1503 of SEQ ID NO:1.

In another preferred embodiment, the nucleic acid sequence is the glucanotransferase encoding part of the DNA sequence which has been cloned into a plasmid present in *Escherichia coli* DSM 13049, or a variant thereof having at least 70% identity to said DNA sequence. With respect to the variant it is preferred that the variant DNA sequence has at least 75%, at least 80%, at least 85%, at least 90%, at least 95%, at least 96%, at least 97%, at least 98%, or at least 99% identity with the the glucanotransferase encoding part of the DNA sequence which has been cloned into a plasmid present in *Escherichia coli* DSM 13049.

The present invention also encompasses nucleic acid sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode fragments of SEQ ID NO:2 that have glucanotransferase activity.

A subsequence of SEQ ID NO:1 is a nucleic acid sequence encompassed by nucleotides 1 to 1503 SEQ ID NO:1 except that one or more nucleotides from the 5' and/or 3' end have been deleted.

The present invention also relates to isolated nucleic acid sequences encoding a polypeptide of the present invention, which hybridize under low stringency conditions, preferably under medium stringency conditions, more preferably under high stringency conditions, with (i) a complementary strand of the nucleic acid sequence shown as nucleotides 1 to 1503 of SEQ ID NO:1, or (ii) a subsequence of (i) of at least 100 nucleotides. The present invention also relates to complementary strands of (i), (ii), and (iii).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Thermus rubins ATCC 31556 or another or related organism and may, for example, be an allelic or species variant of the polypeptide encoding region of the nucleic acid sequence.

An isolated nucleic acid sequence can, for example, be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

For purposes of the present invention, the degree of identity between two nucleic acid sequences is determined is described above.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For. a general description of nucleotide substitution, see, e.g., Ford et al., 1991, Protein Expression and Purification 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244: 1081–1085). In the latter technique, mutations are introduced at every positively charged residue in the molecule, and the resultant mutant molecules are tested for glucanotransferase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306–312; Smith et al., 1992, Journal of Molecular Biology 224: 899–904; Wlodaver et al., 1992, FEBS Letters 309: 59–64).

Nucleic Acid Constructs

The present invention also relates to nucleic acid constructs comprising a nucleic acid sequence of the present invention operably linked to one or more control sequences capable of directing the expression of the polypeptide in a suitable host cell.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequences include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the E. coli lac operon, Streptomyces coelicolor agarase gene (dagA), Bacillus subtilis levansucrase gene (sacB), Bacillus licheniformis alpha-amylase gene (amyL), Bacillus stearothermophilus maltogenic amylase gene (amyM), Bacillus amyloliquefaciens alpha-amylase gene (amyQ), Bacillus licheniformis penicillinase gene (penP), Bacillus subtilis xylA and xylB genes, and prokaryotic beta-lactamase gene (Villa-Kamaroff et al., 1978, Proceedings of the National Academy of Sciences USA 75: 3727–3731), as well as the tac promoter (DeBoer et al., 1983, Proceedings of the National Academy of Sciences USA 80: 21–25). Further promoters are described in "Useful proteins from recombinant. bacteria" in Scientific American, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terrninus of the nucleic acid sequence and which, when transcribed, is recognized by the host cell as a signal to add polyadenosine residues to transcribed mRNA. Any polyadenylation sequence which is flnctional in the host cell of choice may be used in the present invention.

Preferred polyadenylation sequences for filamentous fungal host cells are obtained fromthe genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fuigal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Cost Cells

The present invention also relates to recombinant host cells, comprising a nucleic acid sequence of the invention, which are advantageously used in the recombinant production of the polypeptides.

A vector comprising a nucleic acid sequence of the present invention is introduced into a host cell so that the vector is maintained as a chromosomal integrant or as a self-replicating extra-chromosomal vector as described earlier. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus*, or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thome, 1987, *Journal of Bacteriology* 169: 5771–5278).

The host cell may be a eukaryote, such as a mammalian, insect, plant, or fungal cell. In a preferred embodiment, the host cell is a fingal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fingi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fingal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fingal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenuin, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, the method comprising (a) cultivating a strain from the genus Thermus to produce a supernatant comprising the polypeptide; and (b) recovering the polypeptide. Preferably, the strain is of the species *Thermus rubins*, and more preferably *Thermus rubins* ATCC 31556.

The present invention also relates to a method for producing a polypeptide of the invention, the method comprising (a) cultivating a recombinant host cell as described above under conditions conducive to the production of the polypeptide, and (b) recovering the polypeptide from the cells and/or the culture medium.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide of the present invention having glucanotransferase activity so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a. polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide of the present invention having glucanotransferase activity under conditions conducive for production of the polypeptide; and (b) recovering the polypeptide.

The present invention is further illustrated by the following non-limiting examples.

MATERIALS AND METHODS

Molecular cloning techniques are described in J. Sambrook, E. F. Fritsch, and T. Maniatis, 1989, Molecular Cloning, A Laboratory Manual, 2nd Edition, Cold Spring Harbor, N.Y.

The following commercial plasmids/vectors were used: pT7 Blue (Invitrogen, Netherlands) and pBAD/Myc-HisB (Invitrogen, Netherlands).

The following strains were used for transformantion and protein expression: *E. coli* DH12S (GIBCO BRL, Life Technologies, U.S.A.).

Chemicals used as buffers and substrates were commercial products of at least reagent grade.

Determination of Glucanotransferase Activity

Glucanotransferase activity was determined according to a modified version of the method described by Takaha et al. in *J. Biol. Chem.* 268, 1391–1396 (1993):

Substrate Solution:
1% (w/v) maltotriose dissolved in 20 mM sodium phosphate adjusted to pH 7.0.

Activity Measurement:
(1) Pre-incubate 300 μl substrate solution at 65° C.
(2) Add 50 μl of enzyme solution and incubate at 65° C. for 10 minutes.
(3) Add 50 μl 0.04 N NaOH to terminate the reaction.
(4) Let the solution stand at room temperature for 10 minutes in order to allow α- and β-glucose anomers to achieve equilibrium.
(5) Determine the amount of liberated glucose by the Glucose B-test kit (Wako Pure Chemical Industries, Ltd., Japan).

One unit enzyme activity is defined as the amount of enzyme which releases 1 μmol glucose per minute using the above conditions.

EXAMPLES

Example 1

Preparation of a *Thermus rubins* Glucanotransferase Gene Probe

The primers gt-1 and gt-5 were designed based on the other published glucanotransferase genes and used in a polymerase chain reaction (PCR) with genomic DNA from *Thermus rubins*. The above-mentioned glucanotransferase genes have been identified in glucanotransferases from:

*Solanum tuberosum*, Accession number (AC) q06801: *J. Biol. Chem.* 268, 1391–1396 (1993); *Clostridium butyricum* NCIMB7423, AC 137384: *Microbiology* 143(10), 3287–3294 (1997); *Escherichia coli* K-12, AC p15977: *Mol. Microbiol.* 2, 473–479 (1988); Homo sapiens, AC p35573: *J. Biol. Chem.* 267, 9294–9299 (1992); *Haemophilus influenzae*, AC p45176: *Science* 269, 496–512 (1995); *Streptococcus pneumoniae*, AC p29851: *Cell* 31, 327–336 (1982); Synechocystis SP. AC p72785: *DNA Res.* 3, 109–136 (1996); *Thermus aquaticus*, AC AB016244: *Appl. Environ. Microbiol.* 65, 910–915 (1999); and *Borrelia burgdorferi*, AC AE001127: *Nature* 390, 580–586 (1997).

PCR Primers:
gt-1: 5'-GGI GAY ATI CCI ATH TAY RTI GS-3' (SEQ ID NO:3)
gt-5: 5'-RTT RTC RTG IGT ICC IGT RTA-3' (SEQ ID NO:4)
I=inosine
R=A or G
Y=C or T
H=A or T or C
S=G or C PCR was carried out under the following conditions:
70 μl $H_2O$
10 μl 10×reaction buffer
15 μl 25 mM $MgCl_2$
2 μl Taq polymerase (Boehlinger)
2 μl 25 mM dNTPs
1 μl Template (>1 μg)
step 1: 94° C., 75 sec.
step 2: 94° C., 45 sec.
step 3: 52° C., 45 sec.
step 4: 72° C., 90 sec.
(step 2–4: 31 cycles)
step 5: 72° C., 180 sec.

The PCR reaction mixture was separated on an agarose gel, and the expected size of the amplified PCR fragments was calculated from the other published sequence data (see references right above), resulting in approx. 600 bp. These fragments were gel-purified with Suprec™-01(TAKARA), then ligated into a pT7Blue vector using Takara ligation kit ver. 2. The ligation mixture was transformed into *E. coli* DH12S by electroporation. The plasmid from the obtained transformant was checked by restriction enzyme digestion to confirm the size of the *Thermus rubens* glucanotransferase insert.

Example 2

Cloning of the *Thermus rubens* Glucanotransferase Gene

Using the inserted fragment as a *Thermus rubens* glucanotransferase probe, Southern hybridization was performed on digested genomic DNA from *Thermus rubins* to select convenient restriction enzymes for generating subclones. A hybridized KpnI and SacII fragment of 1.8 kb and a hybridized ScaI and Kpn fragment of 1.6 kb were selected for glucanotransferase gene subclones. *Thermus rubins* genomic DNA was digested with KpnI-SacII and ScaI-KpnI, individually. Then these two fractionated fragments were cut out from agarose gels and cloned into pBluescript SK(−). These two libraries were made by transforming the ligated clones into *E. coli* DH12S cells. Colony lift was performed on transformants of these two libraries using Hybond-N+ membranes (Amersham Pharmacia Biotech, Japan), and then hybridized to the DIG-labeled probe. Positive colonies were picked and inserts were checked by PCR. Plasmids from selected colonies were prepared and sequenced by ABI PRISM™ 310 Genetic Analyzer.

Example 3

Construction of Expression Vector

By using the primers ruben-Nco and ruben-Xba, which included a NcoI and XbaI restriction enzyme site, respectively, the whole glucanotransferase gene was amplified from *Thermus rubins* genomic DNA. Cutting the PCR-amplified fragment with NcoI and XbaI allowed directionally cloning into a pBAD/Myc-His A vector digested with NcoI and XbaI. The resulting vector pFuku-ruben (shown in FIG. 1) produced the polypeptide of the invention after transformation in TOP 10 *E. coli* and induction with arabinose.

Primers:

ruben-Nco: PCR primer (forward) for amplification of the *Thermus rubens* glucano-transferase gene. Underlined nucleotides introduce the NcoI site:

5'-GCG<u>CCATGG</u>AACTCCAACGCGCTTTTG-3' (SEQ ID NO:5)

ruben-Xba: PCR primer (reverse) for amplification of the *Thermus rubins* glucano-transferase gene. Underlined nucleotides introduce the XbaI site:

5'-GCG<u>TCTAGA</u>TCAAGCGCGCTGGCTGGCCTC-3' (SEQ ID NO:6)

pBAD/Myc-HisB with the complete *Thermus rubins* glucanotransferase encoding nucleotide sequence was also transformed in *E. coli* DH12S which was deposited at the Deutsche Sammlung von Mikroorganismen und Zellkulturen GmbH as DSM13049 (see below).

Example 4

Expression of the Polypeptide of the Invention

*Thermus rubins* glucanotransferase was heterologously expressed in TOP10 *E. coli* strain transformed with pFuku-ruben. The *E. coli* cells were incubated in SB medium with 100 μg/ml ampicillin at 28° C. overnight. 0.1% arabinose was then added for induction of expression. Cells were spinned down by centrifugation and re-suspended in 20 mM phosphate buffer (pH 6.0). The amount of buffer corresponded to 1/20 of growth media. Cells were then sonicated and debris were removed by centrifugation.

Example 5 pH Profile

The cell extracts were pre-heated to 70° C. for 10 minutes, debris was removed and the pre-treated cell extract was then analyzed for glucanotransferase activity at 65° C., as described above. Two different buffers were used in the preparation of substrate solutions:

4.5 ≦pH≦6.0: sodium acetate buffer 5.5 ≦pH≦8.5: sodium phosphate buffer

Figure 2:
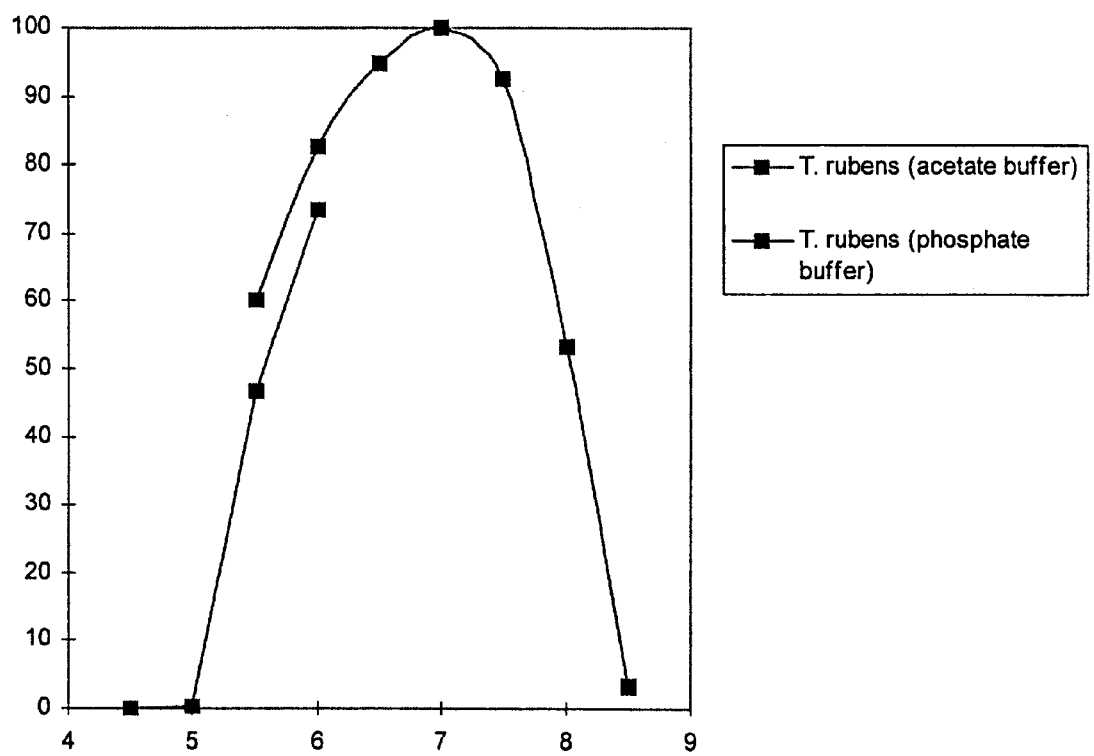
FIG. 2. shows the pH profile of the polypeptide of the invention when tested in acetate buffer and phosphate buffer, respectively.

As it appears from the graph shown in FIG. 2, the pH optimum of the polypeptide of the invention is in the range from 6.5 to 7.5.

Example 6

Temperature Profile

Figure 3:
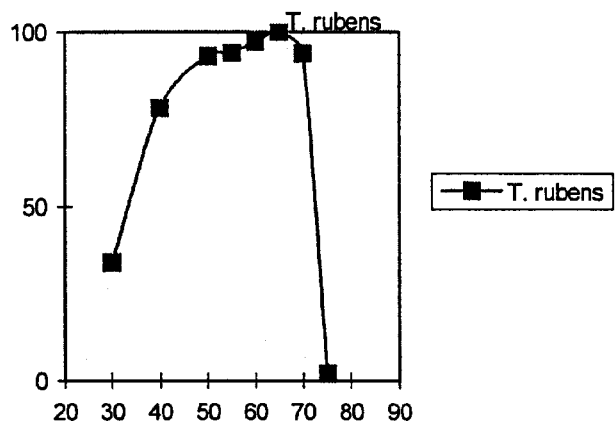
FIG. 3. shows the temperature profile (from 30 to 75° C.) of the polypeptide of the invention.

In order to determine the temperature profile of the enzyme, the cell extracts were pre-heated to 70° C. for 10 minutes, debris was removed and the pre-treated cell extract was then analyzed for glucanotransferase activity in the temperature interval 30–75° C., pH 7.0, as described above. As it appears from the graph shown in FIG. 3, the temperature optimum of the enzyme is in the range from 50° C. to 70° C.

Example 7

Thermal Stability

Figure 4:
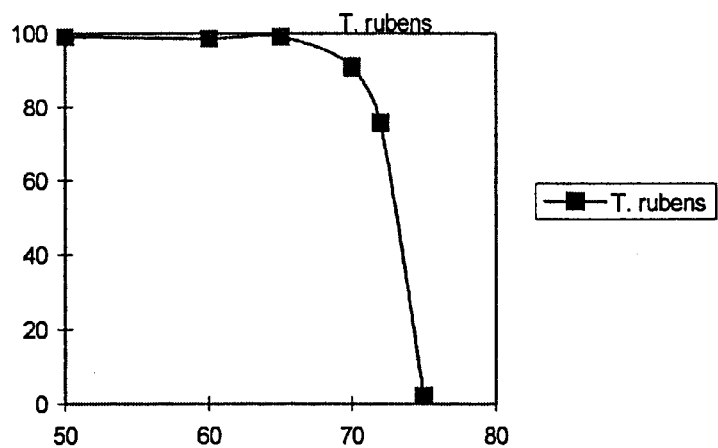
FIG. 4 shows the thermal stability (from 50 to 75° C.) of the polypeptide of the invention.

In order to determine the heat stability of the enzyme, the cell extracts were pre-heated at various temperatures in the interval 50–75° C. for 10 minutes, debris was removed and the pre-treated cell extract was then analyzed for glucanotransferase activity at 65° C., as described above. As it appears from the graph shown in FIG. 4, the enzyme is stable at 70° C. after which the stability of the enzyme is dramatically reduced.

Deposit of Biological Material

The following biological material has been deposited under the terms of the Budapest Treaty with the Deutsche Sammlung von Mikroorganismen und Zellkulturen GmbH, Mascheroder Weg 1 B, D-38124 Braunschweig, Germany, and given the following accession number:

| Deposit | Accession Number | Date of Deposit |
| --- | --- | --- |
| *E. coli* DH12S pFuku-Ruben | DSM 13049 | 20 Sept. 1999 |

What is claimed is:

1. An isolated polypeptide having glucanotransferase activity, selected from the group consisting of:
   (a) a polypeptide having an amino acid sequence which has at least 80% identity with the amino acid sequence shown as amino acids 1 to 501 of SEQ ID NO:2;
   (b) a polypeptide which is encoded by a nucleic acid sequence which hybridizes under medium stringency conditions with
      (i) a complementary strand of the nucleic acid sequence shown as nucleotides 1 to 1503 of SEQ ID NO:1,
   (c) a polypeptide encoded by the glucanotransferase encoding part of the DNA sequence cloned into a plasmid present in *Escherichia coli* DSM 13049, or a polypeptide having at least 80% identity to the polypeptide encoded by the glucanotransferase encoding part of the DNA sequence cloned into a plasmid present in *Escherichia coli* DSM 13049.

2. The polypeptide of claim 1, having an amino acid sequence which has at least 80% identity with the amino acid sequence shown as amino acids 1 to 501 of SEQ ID NO:2.

3. The polypeptide of claim 1, comprising the amino acid sequence shown as amino acids 1 to 501 of SEQ ID NO:2.

4. The polypeptide of claim 1, consisting of the amino acid sequence shown as amino acids 1 to 501 of SEQ ID NO:2 or a fragment thereof.

5. The polypeptide of claim 1, wherein the polypeptide has at least 80% identity with the polypeptide encoded by the glucanotransferase encoding part of the DNA sequence cloned into a plasmid present in *Escherichia coli* DSM 13049.

6. The polypeptide of claim 1, which is encoded by a nucleic acid sequence which hybridizes under medium stringency conditions with
   (i) a complementary strand of the nucleic acid sequence shown as nucleotides 1 to 1503 of SEQ ID NO:1.

7. The polypeptide of claim 1, which retains at least 75% activity after incubation at 67° C., or incubation at 70° C., for 10 min in a 20 mM phosphate buffer, pH 7.0, the activity being measured relative to the activity of the polypeptide after incubation at 65° C. for 10 min in a 20 mM phosphate buffer, pH 7.0.

8. The polypeptide of claim 7, which retains at least 80% activity after incubation at 67° C. for 10 min in a 20 mM phosphate buffer, pH 7.0.

9. The polypeptide of claim 1, which is capable of generating a cyclic glucan by an intramolecular transglycosylation reaction, the substrate being an α-glucan.

10. The polypeptide of claim 1, which is derived from the genus Thermus.

11. The polypeptide of claim 10, which is derived from *Thermus rubins* ATCC 31556.

12. A cleaning or detergent composition comprising the polypeptide as defined in claim 1.

13. A method for removal of starch stains from a hard surface or from laundry, the method comprising contacting the stain-containing hard surface or the stain-containing laundry with the polypeptide defined in claim 1.

14. The polypeptide of claim 1, having an amino acid sequence which has at least 85% identity with the amino acid sequence shown as amino acids 1 to 501 of SEQ ID NO:2.

15. The polypeptide of claim 1, having an amino acid sequence which has at least 90% identity with the amino acid sequence shown as amino acids 1 to 501 of SEQ ID NO:2.

16. The polypeptide of claim 1, having an amino acid sequence which has at least 95% identity with the amino acid sequence shown as amino acids 1 to 501 of SEQ ID NO:2.

17. The polypeptide of claim 1, having an amino acid sequence which has at least 96% identity with the amino acid sequence shown as amino acids 1 to 501 of SEQ ID NO:2.

18. The polypeptide of claim 1, having an amino acid sequence which has at least 97% identity with the amino acid sequence shown as amino acids 1 to 501 of SEQ ID NO:2.

19. The polypeptide of claim 1, having an amino acid sequence which has at least 98% identity with the amino acid sequence shown as amino acids 1 to 501 of SEQ ID NO:2.

20. The polypeptide of claim 1, having an amino acid sequence which has at least 99% identity with the amino acid sequence shown as amino acids 1 to 501 of SEQ ID NO:2.

21. The polypeptide of claim 1, which is encoded by a nucleic acid sequence which hybridizes under high stringency conditions with a complementary strand of the nucleic acid sequence shown as nucleotides 1 to 1503 of SEQ ID NO:1.

* * * * *